United States Patent [19]

Summers, Jr.

[11] Patent Number: 4,608,390
[45] Date of Patent: Aug. 26, 1986

[54] LIPOXYGENASE INHIBITING COMPOUNDS

[75] Inventor: James B. Summers, Jr., Libertyville, Ill.

[73] Assignee: Abbott Laboratories, North Chicago, Ill.

[21] Appl. No.: 727,465

[22] Filed: Apr. 26, 1985

[51] Int. Cl.$^4$ .................. C07C 83/10; A61K 31/185; A61K 31/04
[52] U.S. Cl. ................ 514/575; 260/500.5 H; 260/501.1; 260/501.11; 514/555
[58] Field of Search ............ 260/500.5 H, 501.1, 260/501.11; 514/575, 555

[56] References Cited

U.S. PATENT DOCUMENTS

| | | | |
|---|---|---|---|
| 2,397,508 | 4/1946 | Rougult et al. | 260/500.5 H |
| 3,900,514 | 8/1975 | Chappelow et al. | 260/500.5 H |
| 3,978,116 | 8/1976 | Fried et al. | 260/500.5 H |
| 4,109,013 | 8/1978 | Grill et al. | 260/500.5 H |

Primary Examiner—J. E. Evans
Attorney, Agent, or Firm—Robert W. Stevenson; Martin L. Katz; Michael J. Roth

[57] ABSTRACT

Compounds of the formula

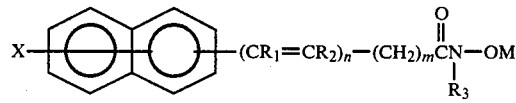

where
X is selected from hydrogen, $C_1$ to $C_{22}$ alkyl or alkenyl, or an electron withdrawing group;
n=0 or 1 and m=0, 1, 2 or 3; but n and m are not O simultaneously;
$R_1$ and $R_2$ independently are hydrogen, $C_1$ to $C_6$ alkyl, an electron withdrawing group, or $R_4$;
$R_3$ is H, $C_1$ to $C_6$ alkyl or cycloalkyl, or $R_4$; and
$R_4$ independently at each occurrence, has the formula

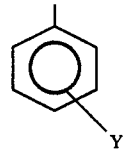

where Y is hydrogen or an electron withdrawing group;
and wherein M is a pharmaceutically acceptable cation, are potent inhibitors of lipoxygenase enzymes.

21 Claims, No Drawings

LIPOXYGENASE INHIBITING COMPOUNDS

TECHNICAL FIELD

This invention relates to novel organic compounds which inhibit lipoxygenase enzymes. It also relates to methods of making such compounds, and to methods of inhibiting lipoxygenase enzymes in human and animal hosts in need of such treatment.

The lipoxygenases are a family of enzymes which catalyze the oxidation of arachidonic acid. The enzyme 5-lipoxygenase converts arachidonic acid to 5-hydroperoxyeicosatetraenoic acid (5-HPETE). This is the first step in the metabolic pathway which yields 5-hydroxyeicosatetraenoic acid (5-HETE) and the leukotrienes (LTs). Similarly, 12- and 15-lipoxygenase convert arachidonic acid to 12- and 15-HPETE, respectively. Biochemical reduction of 12-HPETE leads to 12-HETE, while 15-HETE is the precursor of the class of compounds known as lipoxins.

A variety of biological effects are associated with these products of lipoxygenase activity, and many are implicated as mediators in various disease states. The C4 and D4 LTs are potent constrictors of human bronchial smooth muscle in vitro, and induce bronchoconstriction when administered as aerosols to non-asthmatic human volunteers. LTB4 and 5-HETE are potent chemotactic factors for inflammatory cells such as polymorphonuclear leukocytes. They are also found in the synovial fluid of patients with rheumatoid arthritis. The biological activity of the LTs has been reviewed by Samuelsson, *Angew. Chem. Int. Ed. Eng.*, 21, 902 (1982), and by Green and Lambeth, *Tetrahedron*, 39, 1687 (1983), the disclosures of which are incorporated herein by reference.

The product 12-HETE has been found at high levels in the epidermal tissue of patients with psoriasis. The lipoxins have been shown to stimulate lysozomal enzyme and superoxide ion release from neutrophils.

Thus, lipoxygenase enzymes play an important role in the biosynthesis of mediators of asthma, allergy, arthritis, psoriasis, and inflammation. Blocking these enzymes interrupts the biochemical pathway involved in these disease states.

BACKGROUND ART

Relatively few compounds are known from the prior art which are inhibitors of lipoxygenase enzymes. Among the lipoxygenase inhibitors known to the art are: AA-861, a 5-lipoxygenase inhibitor, disclosed in U.S. Pat. No. 4,393,075, issued July 12, 1983 to Terao et al.; pyrazolo pyridines, which are 5-lipoxygenase inhibitors, disclosed in European Patent Application of Irikura et al., Ser. No. 121,806, published Oct. 17, 1984; arachidonyl hydroxamic acid, a 5-lipoxygenase inhibitor, disclosed in E. J. Corey et al., *J. Am. Chem. Soc.*, 106, 1503 (1984) and European Patent Application of P. H. Nelson, Ser. No. 104,468, published Apr. 4, 1984; BW755C, inhibitor of 5- and 12-lipoxygenases, disclosed in Radmark et al., *FEBS Lett.*, 110, 213 (1980); nordihydroguaiaretic acid, an inhibitor of 5- and 15-lipoxygenases, disclosed in Morris et al., *Prostaglandins*, 19, 371 (1980); REV-5901, a 5-lipoxygenase inhibitor, disclosed in Coutts, Meeting Abstract 70, *Prostaglandins and Leukotrienes '84*; alkyl quinoline N-oxides, as disclosed in the German application of Kyowa Hakko Kogyo KK, abstracted in Derwent Abstract 884-289705/47, and stated to be useful for the treatment of bronchial asthma, atopic dermatitis, inflammation, edema, hypertension, ischemic brain disease and arteriosclerosis; and benzoxaprofen, disclosed in J. Walker, *Pharm. Pharmacol.*, 31, 778 (1979).

It would be useful to have compounds which are more potent inhibitors of these enzymes. In addition, a number of compounds identified as having some lipoxygenase inhibitory activity are structurally based on highly unsaturated lipid compounds which are derivatives of arachidonic acid. Such compounds are highly susceptible to oxidation in vitro and to breakdown by conventional pathways of lipid metabolism in vivo. Thus, as well as having the desired potency, it would be desirable to have agents which are relatively simple in structure, and relatively resistant to oxidation and metabolism.

It is an object of the present invention to provide compounds which are highly potent inhibitors of lipoxygenase enzymes.

It is another object of this invention to provide compounds having structures which are simpler and more stable than prior art compounds having lipid-like structures.

It is yet another object of this invention to provide compounds which inhibit lipoxygenase activity in vivo.

These and other objects of this invention will be evident from the following disclosure.

DISCLOSURE OF THE INVENTION

The present invention provides compounds of the formula

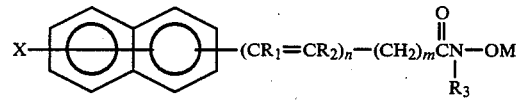

where
X is selected from hydrogen, $C_1$ to $C_{22}$ alkyl or alkenyl, or an electron withdrawing group;
n=0 or 1 and m=0, 1, 2 or 3, but n and m are not 0 simultaneously;
$R_1$ and $R_2$ independently are hydrogen, $C_1$ to $C_6$ alkyl, an electron withdrawing group, or $R_4$;
$R_3$ is H, $C_1$ to $C_6$ alkyl or cycloalkyl or $R_4$; and
$R_4$ independently at each occurrence, has the formula

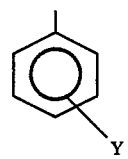

where Y is hydrogen or an electron withdrawing group;
and wherein M is a pharmaceutically acceptable cation.

The term "electron withdrawing group" as used herein refers to radicals which are more electronegative than hydrogen, including, but not limited to $NO_2$, CN, $CF_3$, COOH, F, Cl, Br, I, COOR, SOOR, and the like.

The terms "alkyl", "cycloalkyl" and "alkenyl" are used herein to mean straight and branched chain saturated, cyclic and unsaturated radicals, respectively, including, but not limited to, methyl, ethyl, ethenyl, n-propyl, isopropyl, 2-propenyl, n-butyl, sec-butyl, isobutyl, tert-butyl, 1-, 2-, or 3-butenyl, cyclopropyl, cyclohexyl, ethylcyclohexyl, and the like.

The term "pharmaceutically acceptable cation" is used herein to mean hydrogen and the nontoxic cations based on the alkali and alkaline earth metals, such as sodium, lithium, potassium, calcium, magnesium, and the like, as well as those based on nontoxic ammonium, quaternary ammonium, and amine cations, including, but not limited to, ammonium, tetramethylammonium, tetraethylammonium, methylamino, dimethylamino, trimethylamino, triethylamino, and ethylamino cations, and the like.

Method of Treatment

This invention also provides a method of inhibiting 5-, 12- and/or 15-lipoxygenase activity in a human or lower animal host in need of such treatment, which method comprises administration to the human or lower animal host an amount of a compound of this invention effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intramuscular, intrathecal, intraarticular, epidural and intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from 0.001 to 100 mg/kg body weight daily and more usually 0.01 to 10 mg/kg/day. Dosage unit compositions may contain such amounts or such submultiples thereof as may be used to make up the daily dose. It will be understood, however, that the specific dose level for any particular patient will depend upon a variety of factors including the activity of the specific compound employed, the age, body weight, general health, sex, diet, time and route of administration, rates of absorption and excretion, combination with other drugs and the severity of the particular disease being treated.

Formulation of Pharmaceutical Compositions

This invention also provides compositions in unit dosage form for the inhibition of 5-, 12- and/or 15-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the compositions of this invention, as available in the pharmaceutical arts. Injectable preparations, such as sterile injectable aqueous or oleaginous solutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile, nonpyrogenic water or 1,3-butanediol. Among the other acceptable vehicles and solvents that may be employed are 5% dextrose injection, Ringer's injection and isotonic sodium chloride injection (as described in the USP/NF). In addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compounds of this invention can be prepared by mixing the drug with suitable nonirritating excipients such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

Synthesis of Compounds

Compounds of this invention wherein m is 0 and n is 1 can be prepared according to the reaction sequence below. Although this sequence illustrates the synthesis of compounds in which $R_1$, $R_2$ and $R_3$ are hydrogen, it will be appreciated from the schematic illustration that other compounds of this invention can be prepared in the same manner using the appropriate starting materials.

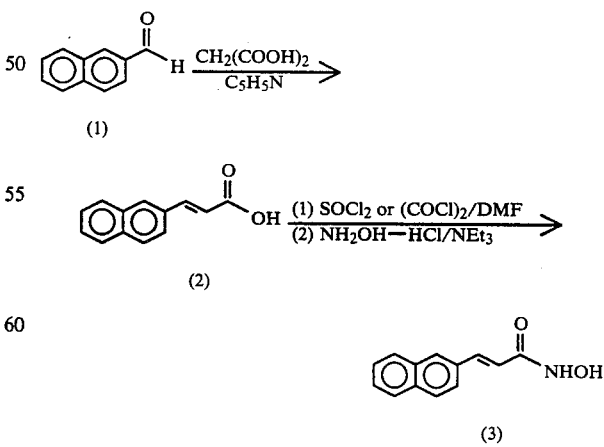

Naphthyl acrylic acid (2) is prepared in a Doebner condensation of 2-naphthaldehyde (1) with malonic acid in pyridine. The acid is converted to the hydroxamic acid (3) by first treating (2) with either thionyl chloride or oxalyl chloride and dimethyl formamide in methylene chloride followed by reaction with hydroxylamine hydrochloride in the presence of triethylamine. A mixture of tetrahydrofuran and water (2:1 v/v) is used as the solvent for the latter reaction.

In addition to the method described above, compounds of this invention where m is 0, n is 1 and $R_3$ is $R_4$ can be prepared according to the following alternative reaction sequence:

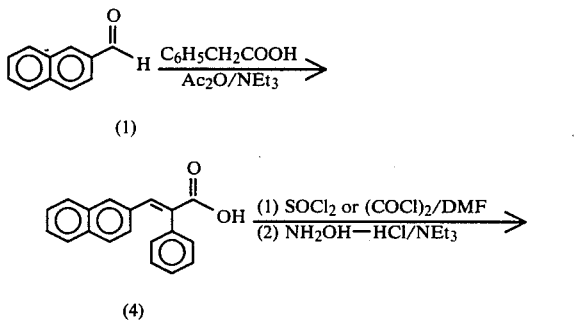

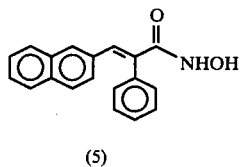

Phenyl acetic acid is condensed with 2-naphthaldehyde (1) in the presence of acetic anhydride and triethylamine to afford the acrylic acid (4). This is then converted to the hydroxamic acid (5) as described above.

In addition to the foregoing methods, compounds of this invention in which m is 0, n is 1 and $R_1$ is $C_1$ to $C_6$ alkyl can be prepared according to the following reaction scheme:

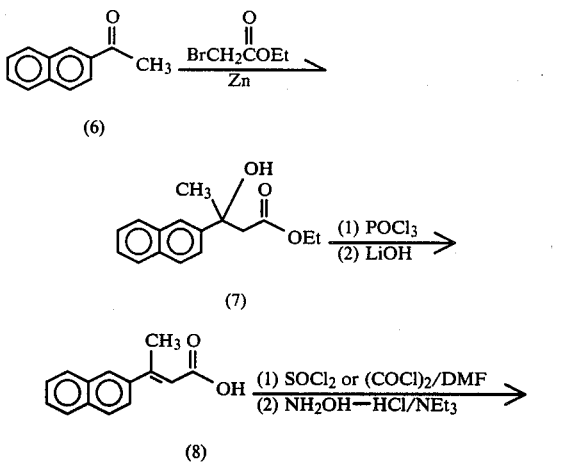

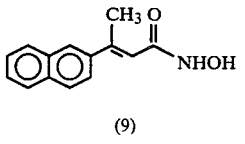

A Reformatsky reaction between ethyl bromoacetate and 2-acetylnaphthalene (6) afford the hydroxy ester (7). After dehydration with phosphorus oxychloride and hydrolysis with lithium hydroxide, acrylic acid (8) is converted to the hydroxamic acid (9) as described above.

Compounds of this invention where n is 1 and m is 1, 2 or 3 can be prepared in the following manner:

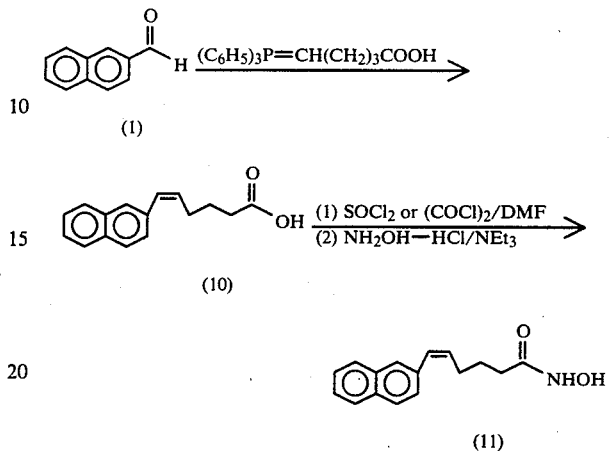

Naphthaldehyde (1) is converted to carboxylic acid (10) in a Wittig reaction with 5-(triphenylphosphino)-pentanoic acid and then to the hydroxamic acid (11) as described above.

Compounds prepared according to the foregoing schemes are converted to compounds where n is 0 and m is 2 or 3 by the reaction sequence below.

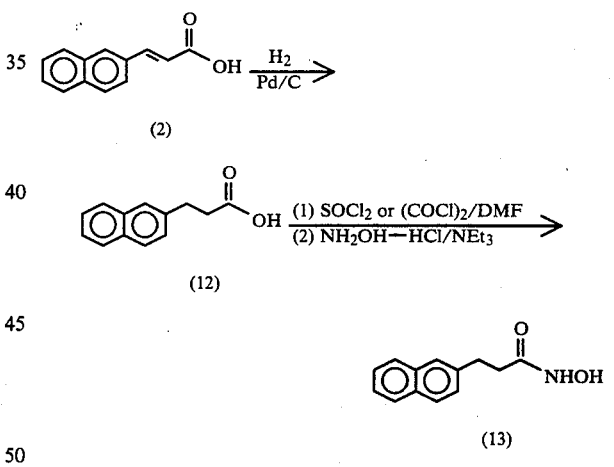

The unsaturated acid (2) is catalytically hydrogenated over 5% palladium on carbon. The resulting saturated acid (12) is converted to the hydroxamic acid (13) as described above.

The following examples further illustrate the synthesis and use of compounds according to this invention.

EXAMPLE 1

3-(2-naphthyl)acrylohydroxamic acid a. 3-(2-naphthyl)acrylic acid

Malonic acid (7.5 g, 72.1 mmole) and 2-naphthaldehyde (5.0 g, 32.0 mmole) were dissolved in pyridine (20 mL) and refluxed for 1 hour. After cooling to room temperature, the reaction mixture was poured into 2N HCl solution (200 mL). The product precipitated immediately. It was collected by filtration and recrystallized from aqueous ethanol (200 mL ethanol/50 mL water) to give colorless needles (5.2 g, 82%).

Melting point: 207°–208° C.

NMR (300 MHz, DMSO-$d_6$): 6.68 (d, 1H, vinyl); 7.50–8.20 (m, 8H, aromatic); 12.5 (brs, 1H, COOH).

IR (KBr): 3900 (Vbr, OH), 1700 (S, C=O).

Mass Spectrum: 198 (M+), 181 (M+—OH), 153 (M+—COOH), 127 (Naph+).

b. 3-(2-naphthyl)acrylohydroxamic acid

Oxalyl chloride (6.4 g, 50.4 mmole) was added under nitrogen at 0° C. to a solution of the carboxylic acid of part (a), above (4.0 g, 20.1 mmole) and dimethyl formamide (DMF) (1.47 g, 20.1 mmole) in methylene chloride (100 mL). Extensive gas evolution was noted. This solution was stirred for 20 minutes and was added at 0° C. to a mixture of hydroxylamine hydrochloride (5.6 g, 80.7 mmole) and triethylamine (17 mL, 121 mmole) in THF (20 mL) and water (10 mL). After stirring for 1 hour, the mixture was then poured into 2N HCl solution (50 mL) and extracted into methylene chloride (50 mL). The organic phase was washed again with 2N HCl (50 mL), dried with brine and MgSO$_4$, and the solvent was evaporated. The resulting product was recrystallized from methanol/water to obtain white crystals.

Melting point: 145°–146° C., (dec).

NMR (300 MHz, DMSO-$d_6$): 56.6 (d, 1H, vinyl); 7.3–8.0 (m, 8H, aromatic+vinyl); 9.4 (brs, 1H, OH); 10.5 (brs, 1H, NH).

IR (KBr): 3250 (br, OH), 1675 (s, C=O).

Mass Spectrum: 213 (M+), 196 (M+—OH), 181 (M+—NHOH), 153 (M+—CONHOH).

EXAMPLE 2

N-methyl 3-(2-naphthyl)acrylohydroxamic acid

Using the procedure of Example (1), part (b), but using N-methyl hydroxylamine hydrochloride, the desired compound was obtained.

Melting point: 138°–140° C.

NMR (60 MHz, DMSO-$d_6$): 4.92 (s, 3H, NCH$_3$); 7.2–8.0 (m, 9H, aromatic+vinyl); 9.6 (brs, 1H, OH).

IR (KBr): 3000–3300 (vbr, OH), 1690 (s, C=O).

Mass Spectrum: 227 (M+), 181 (M+—NCH$_3$OH), 152 (M+—CONCH$_3$OH—H).

$^{13}$C-NMR (22.5 MHz, CD$_3$OD): 36.8 (s), 117.6 (d), 124.6 (d), 127.7 (d), 128.1 (d), 128.7 (d), 129.5 (d), 130.5 (d), 134.0 (s), 234.9 (s), 135.5 (s), 243.5 (d), 168.4 (s).

EXAMPLE 3

N-isopropyl 3-(2-naphthyl)acrylohydroxamic acid

Using the procedure of Example (1), part (b), but using N-isopropyl hydroxylamine hydrochloride, the desired compound was obtained.

Melting point: 184°–185° C.

NMR (300 MHz, DMSO-$d_6$): 1.15 [d, 6H, (CH$_3$)$_2$]; 4.72 (m, 1H, CH); 7.33–8.15 (m, 9H, aromatic+vinyl); 9.65 (brs, 1H, OH).

IR (KBr): 3170 (br, OH), 1685 (s, C=O).

Mass Spectrum: 255 (M+), 181 (M+—NiPrOH), 153 (M+—CONiPrOH).

EXAMPLE 4

N-cyclohexyl 3-(2-naphthyl)acrylohydroxamic acid

Using the procedure of Example (1), part (b), but using N-cyclohexyl hydroxylamine hydrochloride, the desired compound was obtained.

Melting point: 187°–188° C.

NMR (300 MHz, DMSO-$d_6$): 1.0–1.85 (m, 10H, cyclohex), 4.30 (m, 1H, —CH—) 7.33–8.15 (m, 9H, aromatic+vinyl); 9.7 (brs, 1H, OH).

IR (KBr): 3140 (br, OH), 1675 (S, C=O).

Mass Spectrum: 295 (M+), 181 (M+—NROH), 153 (M+—CONROH).

EXAMPLE 5

N-phenyl 3-(2-naphthyl)acrylohydroxamic acid

Using the procedure of Example (1), part (b), but using N-phenyl hydroxylamine hydrochloride, the desired compound was obtained.

Melting point: 175°–177° C.

NMR (300 MHz, DMSO-$d_6$): 7.15–8.25 (m, 14H, aromatic+vinyl); 10.93 (s, 1H, OH).

IR (KBr): 3130 (vbr, OH); 1690 (C=O).

Mass Spectrum: 289 (M+); 181 (M+—NROH); 153 (M+—CONROH).

EXAMPLE 6

2-methyl-3-(2-naphthyl)acrylohydroxamic acid

Using the procedure of Example (1), part (b), but using N-phenyl hydroxylamine hydrochloride, the desired compound was obtained.

NMR (300 MHz, CD$_3$OD): 2.14 (s, 3H, CH$_3$); 7.34–7.90 (m, 8H, aromatic+vinyl).

Mass Spectrum: 227 (M+), 210 (M+—OH), 195 (M+—NHOH), 165 (M+—CONHOH).

EXAMPLE 7

2,N-dimethyl-3-(2-naphthyl)acrylohydroxamic acid

Using the procedure of Example (1), but using methyl malonic acid and N-methyl hydroxylamine hydrochloride, the desired compound was obtained.

NMR (300 MHz, CD$_3$OD): 2.20 (s, 3H, CH$_3$); 3.35 (s, 3H, NCH$_3$); 6.92 (s, 1H, vinyl); 7.47–7.90 (m, 7H, aromatic).

Mass Spectrum: 241 (M+), 195 (M+—NCH$_3$OH), 165 (M+—CONCH$_3$OH).

EXAMPLE 8

N-methyl-3-(2-naphthyl)-2-phenyl acrylohydroxamic acid a. 3-(2-naphthyl)-2-phenyl acrylic acid A mixture of 2-naphthaldehyde (5 g, 32 mmole), phenylacetic acid (4.4 g, 32 mmole), triethylamine (5 mL) and acetic anhydride (10 mL) were refluxed for 5 hours. The solution was poured into 2N HCl (150 mL) and a precipitate formed immediately. This was recrystallized from 50% aqueous ethanol to yield 7.8 g (89% yield) of a white power.

Mass spectrum: 274 (M+).

b. N-methyl-3-(2-naphthyl)-2-phenyl acrylohydroxamic acid

The material from part (a) above was converted to the desired compound using the procedure in Example 1, part (b), but using N-methyl hydroxylamine hydrochloride.

NMR (300 MHz, acetone-d$_6$): 3.33 (s, 3H, NCH$_3$); 7.04 (s, 1H, vinyl); 7.13–7.84 (m, 12H, aromatic); 8.97 (brs, 1H, OH).

Mass Spectrum: 303 (M$^+$), 257 (M$^+$—NCH$_3$OH), 229 (M$^+$—CONCH$_3$OH).

EXAMPLE 9

N-methyl-3-(2-naphthyl)-2-(4-fluorophenyl)acrylohydroxamic acid

Using the procedure of Example 8, but using 4-fluorophenylacetic acid, the desired compound was obtained.

Melting Point: 132°–134° C.

NMR (300 MHz, acetone-d$_6$): 3.34 (s, 3H, NCH$_3$); 7.05–7.85 (m, 12H, aromatic+vinyl).

Mass spectrum: 321(M$^+$); 275 (M$^+$—NCH$_3$OH); 247 (M$^+$—CONCH$_3$OH).

EXAMPLE 10

N-methyl-3-(2-naphthyl)-2-(4-chlorophenyl)acrylohydroxamic acid

Using the procedure of Example 8, but using 4-chlorophenylacetic acid, the desired compound was obtained.

Melting Point: 140°–142° C.

NMR (300 MHz, acetone-d$_6$): 3.35 (s, 3H, NCH$_3$); 7.1–7.85 (m, 12H, aromatic+vinyl).

Mass spectrum: 337 (M$^+$); 291, 263, 228.

EXAMPLE 11

N-methyl-3-(2-naphthyl)-2-(4-bromophenyl)acrylohydroxamic acid

Using the procedure of Example 8, but using 4-bromophenylacetic acid, the desired compound was obtained.

Melting Point: 118°–120° C.

NMR (300 MHz, acetone-d$_6$): 3.32 (s, 3H, NCH$_3$); 7.09–7.85 (m, 12H, aromatic+vinyl).

Mass spectrum: 381, 383 (M$^+$); 337, 339 (M$^+$—NCH$_3$OH); 309 (M$^+$—CONCH$_3$OH).

EXAMPLE 12

3,N-dimethyl-3-(2-naphthyl)acrylohydroxamic acid a. 3-methyl-3-(2-naphthyl)acrylic acid The desired compound was prepared using the method of Rohman and Gastaminza, Rec. Trav. Chim., 81, 645, (1962).

b. 3,N-dimethyl-3-(2-naphthyl)acrylohydroxamic acid

The material from part (a) above was converted to the desired compound using the procedure in Example (1), part (b) but using N-methyl hydroxylamine hydrochloride.

Melting Point: 129°–131° C.

NMR (300 MHz, CDCl$_3$): 2.55 (s, 3H, CH$_3$); 3.45 (s, 3H, CH$_3$); 6.35 (s, 1H, vinyl); 7.47–7.92 (m, 7H, aromatic).

IR: (CDCl$_3$): 3200 (OH); 1590, 1620 (s, C=O).

Mass spectrum: 241 (M$^+$); 225 (M$^+$—O); 195 (M$^+$—CONCH$_3$OH).

EXAMPLE 13

N-methyl-3-(3-nitro-2-naphthyl)acrylohydroxamic acid

Using the procedure in Example 1, but using 3-nitro-2-naphthaldehyde and N-methyl hydroxylamine hydrochloride, the desired compound was obtained.

Melting Point: 163°–164° C. (dec).

NMR (300 MHz, DMSO-d$_6$): 3.34 (s, 3H, CH$_3$); 7.33 (d, 1H, vinyl); 7.7–7.9 (s, 3H, vinyl+aromatic); 8.15–8.25 (m, 2H, aromatic); 8.47 (s, 1H, aromatic); 8.81 (s, 1H, aromatic); 10.23 (s, 1H, OH).

IR (KBr): 3170 (OH); 1650, 1590 (C=O).

Mass spectrum: 272 (M$^+$); 226, 209, 196, 180, 152.

EXAMPLE 14

N-methyl-3-[7-(1-heptenyl)-2-naphthyl]acrylohydroxamic acid

Using the procedure in Example 1, but using 7-(1-heptenyl)-2-naphthaldehyde and N-methyl hydroxylamine hydrochloride, the desired compound was obtained.

NMR (300 MHz, DMSO-d$_6$): 0.88 (t, 3H, CH$_3$); 1.30 (m, 4H, CH$_2$CH$_2$CH$_3$); 1.48 (m, 2H, CH$_2$); 2.25 (q, 2H, E—CH$_2$); 2.38 (q, 2H, Z—CH$_2$); 3.35 (s, 3H, NCH$_3$); 5.77 (dt, 1H, Z—=CHCH$_2$); 6.47 (dt, 1H, E: =CHCH$_2$); 6.57 (d, 2H, Np—CH=); 7.30–8.15 (m, 8H, aromatic+vinyl); 10.15 (s, 1H, OH).

IR (KBr): 3170 (OH); 1650, 1590 (C=O).

Mass spectrum: 323 (M$^+$); 277 (M$^+$—CH$_3$NOH).

EXAMPLE 15

N-methyl-3-(1-naphthyl)acrylohydroxamic acid

Using the procedure in Example 1, but using 1-naphthaldehyde and N-methyl hydroxylamine hydrochloride, the desired compound was obtained.

NMR (300 MHz, DMSO-d$_6$): 3.33 (s, 3H, NCH$_3$); 7.80–8.30 (m, 9H, aromatic+vinyl); 10.17 (s, 1H, OH).

IR (KBr): 3130 (OH), 1640 (C=O).

Mass Spectrum: 227 (M$^+$), 181 (M$^+$—NHOH) 153 (M$^+$—CONHOH).

EXAMPLE 16

N-methyl-3-(4-nitro-1-naphthyl)acrylohydroxamic acid

Using the procedure of Example 1 with 4-nitro-1-naphthaldehyde and N-methyl hydroxylamine, the desired compound was obtained.

Melting Point: 164°–166° C. (dec).

NMR (300 MHz, DMSO-d$_6$): 3.25 (s, 3H, NCH$_3$); 7.4 (d, 1H, vinyl); 7.80–8.05 (m, 3H, aromatic); 8.23–8.45 (m, 3H, aromatic); 10.30 (brs, 1H, OH).

IR (KBr): 3100 (OH), 1650, 1590 (C=O).

Mass Spectrum: 272 (M$^+$), 255, 243, 226, 180.

EXAMPLE 17

Z-6-(2-naphthyl)hex-5-enohydroxamic acid a. Z-6-(2-naphthyl)hex-5-enoic acid

Triphenyl (5-carboxypentyl)phosphonium bromide (937 mg, 2.1 mmole) and 2-napthaldehyde (300 mg, 1.92 mmole) were dissolved in DMSO (50 mL, freshly distilled from CaH$_2$) and potassium t-butoxide (540 mg, 4.8 mmole) was added. After stirring for 30 minutes the reaction was quenched with saturated NH$_4$Cl solution (25 mL) and poured into ether. The ether layer was dried with saturated NaCl and MgSO$_4$ and the solvent was evaporated. The resulting 1:1 mixture E/Z isomers were separated with flash chromatography eluting with ether/hexane/formic acid (10:89:1).

NMR (CDCl$_3$, 300 MHz): 7.35–7.85, (m, 7H, aromatic); 6.6, (d, 1H, Ar—CH=); 5.72, (dt, 1H, =CH—CH$_2$), 2.77, (quar, 2H, =CH—CH$_2$); 2.40, (t, 2H, CH$_2$—COOH); 1.83, (m, 2H, CH$_2$—CH$_2$—CH$_2$).

Mass spectroscopy: 240 (M+), 167 (M+—CH$_2$CH$_2$COOH).

b. Z-6-(2-naphthyl-hex-5-enohydroxamic acid

The Z-6-(2-naphthyl)hex-5-enoic acid of the preceding paragraph was converted to the corresponding hydroxamic acid using the procedure of Example 1, part b.

NMR (DMSO-d$_6$, 300 MHz): 10.35, (s, 1H—OH); 8.68 (s, 1H, —NH); 7.4–8.0, (m, 7H, aromatic); 6.6, (d, 1H, Ar—CH=); 5.74, (dt, 1H, =CH—CH$_2$); 2.37, (q, 2H, =CH—CH$_2$); 2.02, (t, 2H, CH$_2$COOH); 1.70 (quint, 2H CH$_2$—CH$_2$—CH$_2$).

Mass spectroscopy: 255 (M+) 181 (M+—CH$_2$CONHOH), 167 (M+—CH$_2$—CH$_2$—CONHOH).

EXAMPLE 18

3-(2-naphthyl)propiohydroxamic acid a. 3-(2-naphthyl)propionic acid

The compound prepared according to Example 1, part (a) was catalytically hydrogenated using 5% palladium on carbon.

Mass spectrum: 200 (M+), 155 (M+—COOH).

b. 3-(2-naphthyl)propiohydroxamic acid

The material from part (a), above, was converted to the desired compound using the procedure of Example 1, part (b).

Melting point: 158°–159° C.

NMR (DMSO-d$_6$): 10.37 (s, 1H, OH); 8.70 (s, 1H, NH); 7.77 (2H, dd); 7.60 (s, 2H); 7.38 (d, 2H); 2.91 (t, 2H); 2.35 (t, 2H).

Mass spectrum: 215 (M+).

EXAMPLE 19

3-(7-methyl-2-napthalene)propiohydroxamic acid

This compound was prepared by the method of Example 18.

NMR (DMSO-d$_6$, 300 MHz): 10.37, s, 1H (OH); 8.70, s, 1H (NH); 7.77, 2H, dd; 7.60 2H, s, 7.38, 2Hd (aromatic); 2.91, 2H, t, (CH$_2$); 2.46, 3H, s, (CH$_3$); 2.35, 2H, t (CH$_2$CO).

IR (KBr): 3200 vbr, 1680.

Mass spectroscopy: 229 (M+) 197 (M+—NHOH) 169 (M+—CONHOH), 155 (M+—CH$_2$CONHOH).

EXAMPLE 20

5-Lipoxygenase IC$_{50}$ Determination

The compounds of this invention are potent inhibitors of 5-, 12- and 15-lipoxygenase. An assay to determine 5-lipoxygenase activity was performed in incubations containing various concentrations of the test compound and the 20,000×G supernatant from 7.5×10$^6$ homogenized RBL-1 cells. Reactions were initiated by the addition of radiolabeled arachidonic acid and terminated by acidification and ether extraction. Reaction products were separated from nonconverted substrate by thin layer chromatography and measured by liquid scintillatiton spectroscopy. Inhibition of 5-lipoxygenase activity was calculated as the ratio of the amounts of product formed in the presence and absence of inhibitor. IC$_{50}$ values were computed as the 50% intercept from linear regression analysis of percentage inhibition versus log concentration plots. Results for compounds of the foregoing Examples are indicated in Table 1, below.

Structural modifications are indicated with reference to the general structure indicated above. The naphthyl group is substituted at the 2-position in each compound, with the exception of the compounds of Examples 15 and 16, where the naphthyl is 1-substituted. M in each instance is hydrogen.

TABLE 1

| Ex. # | n | m | R$_1$ | R$_2$ | R$_3$ | X | Y | IC$_{50}$ μM |
|---|---|---|---|---|---|---|---|---|
| 1 | 1 | 0 | H | H | H | H | — | 0.95 |
| 2 | 1 | 0 | H | H | CH$_3$ | H | — | 0.26 |
| 3 | 1 | 0 | H | H | i-Pr | H | — | 0.15 |
| 4 | 1 | 0 | H | H | c-Hex | H | — | 0.26 |
| 5 | 1 | 0 | H | H | R$_4$ | H | H | 0.20 |
| 6 | 1 | 0 | H | CH$_3$ | H | H | — | 1.8 |
| 7 | 1 | 0 | H | CH$_3$ | CH$_3$ | H | — | 0.47 |
| 8 | 1 | 0 | H | R$_4$ | CH$_3$ | H | H | 0.51 |
| 9 | 1 | 0 | H | R$_4$ | CH$_3$ | H | F | 0.95 |
| 10 | 1 | 0 | H | R$_4$ | CH$_3$ | H | Cl | 1.5 |
| 11 | 1 | 0 | H | R$_4$ | CH$_3$ | H | Br | 1.8 |
| 12 | 1 | 0 | CH$_3$ | H | CH$_3$ | H | — | 0.12 |
| 13 | 1 | 0 | H | H | CH$_3$ | 3-NO$_2$ | — | 0.30 |
| 14 | 1 | 0 | H | H | CH$_3$ | 7-(1-heptenyl) | — | 0.51 |
| 15 | 1 | 0 | H | H | CH$_3$ | H | — | 0.20 |
| 16 | 1 | 0 | H | H | CH$_3$ | 4-NO$_2$ | — | 0.13 |
| 17 | 1 | 3 | H | H | H | H | — | 1.6 |
| 18 | 0 | 2 | H | H | H | H | — | 9.7 |
| 19 | 0 | 2 | — | — | H | 7-CH$_3$ | — | 2.9 |

The inhibitory activities of the compounds of this invention against 12- and 15-lipoxygenase can be determined in the foregoing assay in which 12-lipoxygenase obtained from human platelets, or 15-lipoxygenase obtained from soybean, is substituted for the 5-lipoxygenase-containing cell supernatant fraction. Results of these tests for various of the foregoing compounds are indicated in Table 2.

TABLE 2

| | % Inhibition at Indicated Concentration | | | |
|---|---|---|---|---|
| | 15-lipoxygenase | | 12-lipoxygenase | |
| Ex. # | 100 μM | 10 μM | 100 μM | 10 μM |
| 1 | 19 | 2 | 100 | 92 |
| 2 | 83 | 43 | — | 88 |
| 3 | 63 | 31 | 84 | 75 |
| 4 | 83 | 43 | — | 66 |
| 5 | 30 | 22 | — | 82 |
| 6 | 100 | 45 | — | — |
| 7 | 88 | 37 | — | — |
| 8 | 62 | 38 | — | — |
| 10 | — | — | — | 98 |
| 12 | 88 | 37 | — | — |
| 13 | 49 | 19 | 97 | 81 |
| 14 | 65 | 59 | 98 | 93 |
| 15 | 88 | 29 | 100 | 82 |
| 18 | 31 | 12 | — | — |
| 19 | 33 | 19 | 99 | 82 |

The foregoing is merely illustrative of the invention and is not intended to limit the invention to the disclosed compounds. Variations and changes which are obvious to one skilled in the art are intended to be within the scope and nature of the invention which are defined in the claims.

What is claimed is:

1. A compound of the formula

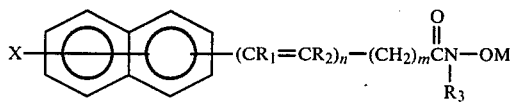

where
X is selected from hydrogen, $C_1$ to $C_{22}$ alkyl or alkenyl, or an electron withdrawing group;
n is 1 and m=0, 1, 2 or 3;
$R_1$ and $R_2$ independently are hydrogen, $C_1$ to $C_6$ alkyl, an electron withdrawing group, or $R_4$;
$R_3$ is H, $C_1$ to $C_6$ alkyl or cycloalkyl, or $R_4$; and
$R_4$ independently at each occurrence, has the formula

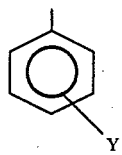

where Y is hydrogen or an electron withdrawing group; and wherein M is a pharmaceutically acceptable cation.

2. A compound according to claim 1 wherein m is 0.

3. A compound according to claim 2 wherein $R_3$ is $C_1$ to $C_6$ alkyl.

4. A compound according to claim 2 wherein $R_3$ is $R_4$.

5. A compound according to claim 3 wherein $R_1$ and $R_3$ are $C_1$ to $C_6$ alkyl and $R_2$ is H.

6. A compound according to claim 3 wherein $R_2$ and $R_3$ are $C_1$ to $C_6$ alkyl and $R_2$ is H.

7. A compound according to claim 1 wherein n is O and M is 3.

8. A compound according to claim 1 wherein the pharmaceutically acceptable cation is a nontoxic cation selected from the group consisting of hydrogen, alkali metal cations, alkaline earth metal cations, and ammonium, quaternary ammonium and amine cations.

9. A method of inhibiting lipoxygenase activity in a human or lower animal host in need of such treatment, comprising administering to the human or lower animal host a compound according to claim 1 in an amount effective to inhibit lipoxygenase activity in the host.

10. A method according to claim 9 wherein the compound is administered orally, parenterally, or topically.

11. A method according to claim 10 wherein the compound is administered at a dosage of from 0.001 to 100 mg/kg body weight per day.

12. A method according to claim 11 wherein the compound is administered at a dosage of from 0.01 to 10 mg/kg body weight per day.

13. A composition in unit dosage form for the inhibition of lipoxygenase activity in a human or lower animal host, comprising a compound according to claim 1 and a pharmaceutical carrier material.

14. A compound of the formula

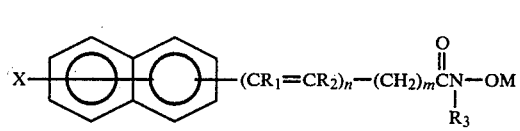

where
X is selected from hydrogen, $C_1$ to $C_{22}$ alkyl or alkenyl, or an electron withdrawing group;
n=0 or 1 and m=0, 1, 2 or 3, but n and m are not 0 simultaneously;
$R_1$ and $R_2$ independently are hydrogen, $C_1$ to $C_6$ alkyl, an electron withdrawing group, or $R_4$;
$R_3$ is $C_1$ to $C_6$ alkyl or cycloalkyl, or $R_4$; and
$R_4$ independently at each occurrence, has the formula

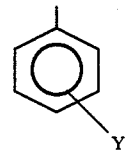

where Y is hydrogen or an electron withdrawing group;
and wherein M is a pharmaceutically acceptable cation.

15. A compound according to claim 14 wherein n is 1 and m is 0.

16. A compound according to claim 15 wherein $R_3$ is $C_1$ to $C_6$ alkyl.

17. A compound according to claim 15 wherein $R_3$ is $R_4$.

18. A compound according to claim 16 wherein $R_1$ and $R_3$ are $C_1$ to $C_6$ alkyl and $R_2$ is H.

19. A compound according to claim 16 wherein $R_2$ and $R_3$ are $C_1$ to $C_6$ alkyl and $R_2$ is H.

20. A compound according to claim 14 wherein n is 0 and M is 3.

21. A method of inhibiting lipoxygenase activity in a human or lower animal host in need of such treatment, comprising administering to the human or lower animal host a compound according to claim 14 in an amount effective to inhibit lipoxygenase activity in the host.

* * * * *